United States Patent
Dalmases Barjoan et al.

(10) Patent No.: US 10,131,630 B2
(45) Date of Patent: Nov. 20, 2018

(54) PROCESS FOR PREPARING (3RS)-3-[(2SR)-(2-CYCLOPENTYL-2-HYDROXY-2-PHENYLACETYL)OXY]-1,1-DIMETHYLPYRROLIDINIUM BROMIDE

(71) Applicant: LABORATORIOS LESVI, S.L., Sant Joan Despí, Barcelona (ES)

(72) Inventors: Pere Dalmases Barjoan, Barcelona (ES); Joan Huguet Clotet, Barcelona (ES); Mª Ángeles Conde Martínez, Inas-Oleiros (ES); Javier Jesús Poza Soto, A Coruna (ES)

(73) Assignee: LABORATORIOS LESVI, S.L., Sant Joan Despi (ES)

( * ) Notice: Subject to any disclaimer, the term of this patent is extended or adjusted under 35 U.S.C. 154(b) by 0 days.

(21) Appl. No.: 15/538,218

(22) PCT Filed: Dec. 4, 2015

(86) PCT No.: PCT/EP2015/078668
§ 371 (c)(1),
(2) Date: Jun. 21, 2017

(87) PCT Pub. No.: WO2016/102174
PCT Pub. Date: Jun. 30, 2016

(65) Prior Publication Data
US 2017/0334848 A1 Nov. 23, 2017

(30) Foreign Application Priority Data
Dec. 24, 2014 (EP) .................................... 14382569

(51) Int. Cl.
*C07D 207/12* (2006.01)

(52) U.S. Cl.
CPC .................................. *C07D 207/12* (2013.01)

(58) Field of Classification Search
CPC ................................................... C07D 207/12
See application file for complete search history.

(56) References Cited

U.S. PATENT DOCUMENTS

| 2,956,062 | A | 10/1960 | Lunsford |
| 6,307,060 | B1 | 10/2001 | Noe et al. |
| 9,926,270 | B2 * | 3/2018 | Shaw ................... C07D 207/12 |

FOREIGN PATENT DOCUMENTS

FI 49713 B 6/1975

OTHER PUBLICATIONS

International Search Report and Written Opinion prepared for PCT/EP2015/078668, dated Feb. 2, 2016, 8 pages.

* cited by examiner

*Primary Examiner* — Sun Jae Yoo
(74) *Attorney, Agent, or Firm* — Barnes & Thornburg LLP

(57) ABSTRACT

The present invention relates to an efficient and environmentally friendly process for preparing (3RS)-3-[(2SR)-(2-cyclopentyl-2-hydroxy-2-phenylacetyl)oxy]-1,1-dimethylpyrrolidinium bromide with high yield and purity suitable for industrial scale applications.

16 Claims, No Drawings

PROCESS FOR PREPARING (3RS)-3-[(2SR)-(2-CYCLOPENTYL-2-HYDROXY-2-PHENYLACETYL)OXY]-1,1-DIMETHYLPYRROLIDINIUM BROMIDE

CROSS-REFERENCE TO RELATED APPLICATIONS

This application is a national stage entry under 35 USC § 371 of PCT International Application Number PCT/EP2015/078668, filed 4 Dec. 2015, which claims priority to European Patent Application Number 14382569.3, filed 24 Dec. 2014, the entire disclosures of which are expressly incorporated by reference herein.

FIELD OF THE INVENTION

The present invention refers to an efficient and environmentally friendly process for the preparation of (3RS)-3-[(2SR)-(2-cyclopentyl-2-hydroxy-2-phenylacetyl)oxy]-1,1-dimethylpyrrolidinium bromide or another pharmaceutically acceptable salt of glycopyrronium, with high yield and purity suitable for industrial scale applications.

BACKGROUND OF THE INVENTION (3RS)-3-[(2SR)-(2-cyclopentyl-2-hydroxy-2-phenylacetyl)oxy]-1,1-dimethylpyrrolidinium bromide, also known as glycopyrronium bromide (compound I) is an M3 antagonist, developed by Sosei R&D in collaboration with Vectura for the treatment of chronic obstructive pulmonary disease (COPD) and asthma. Glycopyrronium bromide is a quaternary ammonium salt (ionic compound) and it is completely ionized between pH 1 and 14. It is a racemic mixture of the 3R,2S and 3S,2R stereoisomers. No optical rotation is seen in solution. Glycopyrronium bromide, which is depicted below, is marketed under the tradename Seebri Breezhaler®.

Compound I

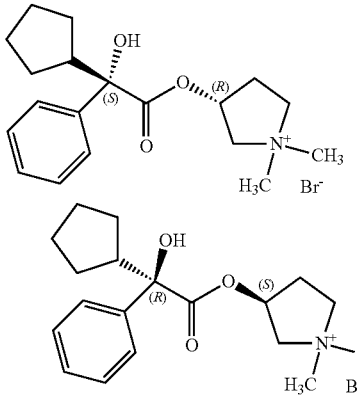

A number of methods of synthesis of glycopyrronium bromide have been reported up to date. Glycopyrronium bromide was first disclosed by the U.S. Pat. No. 2,956,062 to Robins Company, which describes a synthetic approach to the preparation of glycopyrronium bromide, similar molecules and also pharmaceutical composition containing them.

The Finnish patent FI49713 also describes a process for the preparation of the erythro-glycopyrronium bromide. In this patent the enantiomeric forms of glycopyrronium bromide are obtained by the preparation of the intermediate 5-nitroisophthalic acid salts from the mixture of threo- and erythro-1-methyl-3-pyrrolidinyl alpha-cyclopentyl mandelates. These salts are crystalline and may be separated due to their different solubility by digesting them with a suitable organic solvent. Nevertheless, the quality obtained for the 5-nitroisophthalic salts to obtain the final product glycopyrronium bromide is not an acceptable quality for pharmaceutical use as inhaler.

These disadvantages also increase the cost of the final glycopyrronium bromide and the pharmaceutical compositions containing it. In view of the pharmaceutical value of this compound, it is important to obtain an efficient and safe process for the preparation of glycopyrronium bromide in high yields, which can be applied at an industrial scale with low energy and costs. Therefore, there is a need to develop an improved industrially feasible process for the preparation of glycopyrronium bromide, which is more efficient, and can provide glycopyrronium bromide in high chemical and enantiomeric purity and yield and which can be easily performed at industrial scale.

BRIEF DESCRIPTION OF THE INVENTION

The present invention provides an efficient process for preparing glycopyrronium bromide in high yields and high purity and applicable at industrial scale. This process also allows obtaining glycopyrronium bromide without requiring laborious and unfeasible purification steps and yielding a high chemical and enantiomeric purity product which complies with pharmaceutical standards. In addition, the process of the present invention is environmentally friendly.

Accordingly, the present invention provides a process for preparing glycopyrronium bromide (compound I), or another pharmaceutically acceptable salt of glycopyrronium, wherein the process comprises at least the following steps:

a) Contacting 1-methylpyrrolidin-3-yl-2-cyclopentyl-2-hydroxy-2-phenylacetate with 5-nitroisophthalic acid in a mixture of organic solvent and water to yield (RS/SR) 1-methylpyrrolidin-3-yl-2-cyclopentyl-2-hydroxy-2-phenylacetate-5-nitroisophthalic acid salt (compound III);

Compound III

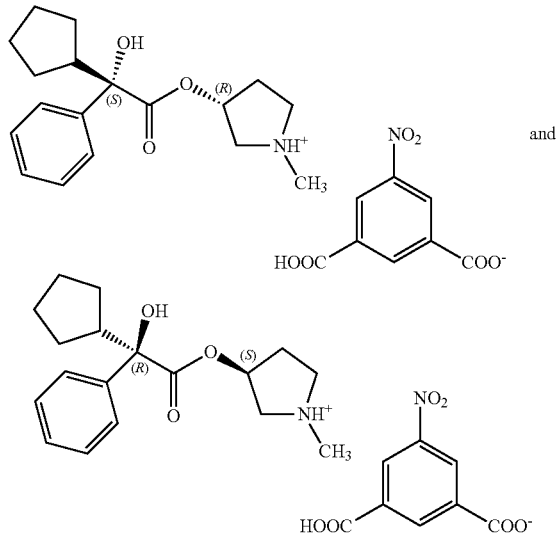

wherein the ratio of organic solvent to water is at most 10:1 (V/V) and the quantity of 5-nitroisophthalic acid is at least 0.5 mol per 1 mol of 1-methylpyrrolidin-3-yl-2-cyclopentyl-2-hydroxy-2-phenylacetate.

b) Isolating the (RS/SR) 1-methylpyrrolidin-3-yl-2-cyclopentyl-2-hydroxy-2-phenylacetate 5-nitroisophthalic acid salt obtained in step a) by filtration.

c) Optionally, purifying the (RS/SR) 1-methylpyrrolidin-3-yl-2-cyclopentyl-2-hydroxy-2-phenylacetate 5-nitroisophthalic acid salt of step b) by means of conventional purification techniques.

d) Treating the (RS/SR) 1-methylpyrrolidin-3-yl-2-cyclopentyl-2-hydroxy-2-phenylacetate 5-nitroisophthalic acid salt of step b) or c) with a base to yield (RS/SR) 1-methylpyrrolidin-3-yl-2-cyclopentyl-2-hydroxy-2-phenylacetate (compound II).

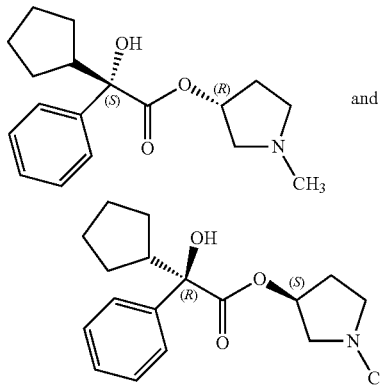

Compound II and e) Contacting the (RS/SR) 1-methylpyrrolidin-3-yl-2-cyclopentyl-2-hydroxy-2-phenylacetate of step d) with methyl bromide to yield glycopyrronium bromide (compound I).

f) Optionally, purifying the glycopyrronium bromide of step e) by means of conventional purification techniques.

g) Optionally, converting the glycopyrronium bromide obtained in step e) or f) into another pharmaceutically acceptable salt or co-crystal.

Definitions

As used herein the term "organic solvent" refers to an organic molecule capable of at least partially dissolving another substance (i.e., the solute). Organic solvents may be liquids at room temperature. In some embodiments, the organic solvent may be formed by the combination of two or more organic solvents.

The term "polar solvent" as used herein means a solvent that tends to interact with other compounds or itself through acid-base interactions, hydrogen bonding, dipole-dipole interactions, or by dipole-induced dipole interactions.

The term "non-polar solvent" as used herein means a solvent that is not a polar solvent. Non-polar solvents interact with other compounds or themselves predominantly through dispersion forces. Non-polar solvents interact with polar solvents mainly through dipole-induced dipole interactions or through dispersion forces.

The term "aprotic solvent" as used herein means any molecular solvent which cannot donate H+, i.e. a compound not having labile hydrogens.

As used herein, the term, "solvent extraction" refers to the process of separating components of a mixture by using a solvent which possesses greater affinity for one component, and may therefore separate said one component from at least a second component which is less miscible than said one component with said solvent.

The term "filtration" refers to the act of removing solid particles greater than a predetermined size from a feed comprising a mixture of solid particles and liquid. The expression "filtrate" refers to the mixture less the solid particles removed by the filtration process. It will be appreciated that this mixture may contain solid particles smaller than the predetermined particle size. The expression "filter cake" refers to residual solid material remaining on a feed side of a filtration element.

The term "purification" as used herein refers to the process of rendering a product clean of foreign elements whereby a purified product can be obtained. The term "industrial purification" refers to purifications which can be carried out on an industrial scale such as solvent extraction, filtration, slurring, washing, phase separation, evaporation, centrifugation or crystallization.

DETAILED DESCRIPTION OF THE INVENTION

The first aspect present of the present invention provides an efficient process for preparing glycopyrronium bromide (compound I), or another pharmaceutically acceptable salt of glycopyrronium, in high yields and high purity and applicable at industrial scale wherein the process comprises at least the following steps:

a) Contacting 1-methylpyrrolidin-3-yl-2-cyclopentyl-2-hydroxy-2-phenylacetate with 5-nitroisophthalic acid in a mixture of organic solvent/water to yield (RS/SR) 1-methylpyrrolidin-3-yl-2-cyclopentyl-2-hydroxy-2-phenylacetate-5-nitroisophthalic acid salt (compound III);

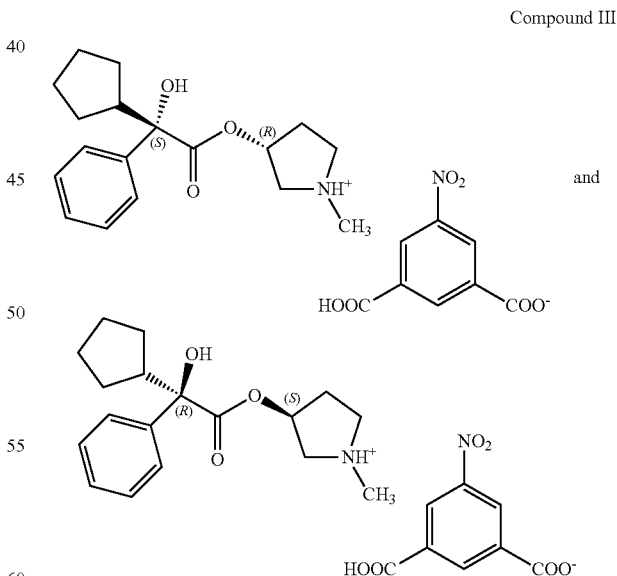

Compound III and wherein the ratio of organic solvent to water is at most 10:1 (V/V) and the quantity of 5-nitroisophthalic acid is at least 0.5 mol per 1 mol of 1-methylpyrrolidin-3-yl-2-cyclopentyl-2-hydroxy-2-phenylacetate. Preferably, the ratio of organic solvent to water is at most 7:1 (V/V), more preferably is at most 5:1 (V/V), most preferably is at most 4:1 (V/V), and the quantity of 5-nitroisophthalic acid is at least 0.5 mol per 1 mol of 1-methylpyrrolidin-3-yl-2-cyclopentyl-2-hydroxy-2-phenylacetate.

The 1-methylpyrrolidin-3-yl-2-cyclopentyl-2-hydroxy-2-phenylacetate is mixed in a mixture of organic solvent and water, optionally heated. 5-nitroisophthalic acid is added to the mixture and is heated to reflux temperature. The mixture is cooled down to yield (RS/SR) 1-methylpyrrolidin-3-yl-2-cyclopentyl-2-hydroxy-2-phenylacetate-5-nitroisophthalic acid salt. The mixture can also be stirred to ease the formation of the (RS/SR) 1-methylpyrrolidin-3-yl-2-cyclopentyl-2-hydroxy-2-phenylacetate-5-nitroisophthalic acid salt.

Suitable organic solvents that may be used for the present invention include, but are not limited to: hydrocarbon solvents, such as n-pentane, n-hexane, n-heptane, n-octane, paraffin, cyclohexane, methylcyclohexane, decahydro-naphthalene, mineral oil, crude oils; aromatic hydrocarbon solvents, such as benzene, toluene, o-xylene, m-xylene, and p-xylene); halogenated hydrocarbon solvents, such as carbon tetrachloride, 1,2-dichloroethane, dichloromethane, chloroform; ester solvents, such as ethyl formate, methyl acetate, ethyl acetate, isopropyl acetate, ethyl malonate; ketone solvents, such as acetone, methyl ethyl ketone, methyl isobutyl ketone, methyl isopropyl ketone; ether solvents, such as diethyl ether, dipropyl ether, diphenyl ether, tetrahydrofuran, 1,4-dioxane; alcohol solvents, such as methanol, ethanol, 1-propanol, 1-butanol, 1-octanol, benzyl alcohol, phenol, trifluoroethanol, glycerol, ethylene glycol, propylene glycol, m-cresol; nitrobenzene, N,N-dimethylformamide, N,N-dimethylacetamide, dimethyl sulfoxide, N-methyl-2-pyrrolidone, acetonitrile or silicone solvents, such as silicone oils, polysiloxanes, cyclosilicones. In an embodiment of the present invention the organic solvent is a polar organic solvent and preferably, the organic solvent is selected from the group consisting of N,N-dimethylformamide, $C_1$-$C_4$ alkyl alcohols, $C_1$-$C_4$-alkyl acetates, ketones and mixtures thereof. In a more preferred embodiment the organic solvent is selected from the group consisting of ethanol, methanol, isopropanol, acetone and mixtures thereof. More preferably, the organic solvent is acetone. In a particular embodiment, the organic solvent may be formed by the combination of two or more organic solvents.

b) Isolating the (RS/SR) 1-methylpyrrolidin-3-yl-2-cyclopentyl-2-hydroxy-2-phenylacetate 5-nitroisophthalic acid salt obtained in step a) by filtration.

The (RS/SR) 1-methylpyrrolidin-3-yl-2-cyclopentyl-2-hydroxy-2-phenylacetate 5-nitroisophthalic acid salt is isolated by filtration. The filtration is carried out over a range of temperatures from 0° C. to 50° C. Preferably, the filtration temperature range is from 10° C. to 30° C. Most preferably, between 15° C. and 25° C., which allows improving the purity of the (RS/SR) 1-methylpyrrolidin-3-yl-2-cyclopentyl-2-hydroxy-2-phenylacetate 5-nitroisophthalic acid salt.

c) Optionally, purifying the (RS/SR) 1-methylpyrrolidin-3-yl-2-cyclopentyl-2-hydroxy-2-phenylacetate 5-nitroisophthalic acid salt of step b) by means of conventional purification techniques and isolating by filtration.

(RS/SR) 1-methylpyrrolidin-3-yl-2-cyclopentyl-2-hydroxy-2-phenylacetate 5-nitroisophthalic acid salt may be purified by mixing the (RS/SR) 1-methylpyrrolidin-3-yl-2-cyclopentyl-2-hydroxy-2-phenylacetate 5-nitroisophthalic acid salt of step b) in a mixture of organic solvent and water and heating to reflux. Afterwards, the mixture is cooled down to 15-25° C. with stirring to obtain a precipitate. The precipitate corresponds to the purified (RS/SR) 1-methylpyrrolidin-3-yl-2-cyclopentyl-2-hydroxy-2-phenylacetate 5-nitroisophthalic acid salt.

(RS/SR) 1-methylpyrrolidin-3-yl-2-cyclopentyl-2-hydroxy-2-phenylacetate-5-nitroisophthalic acid salt is isolated by filtration. The filtration is carried out over a range of temperatures from 0° C. to 50° C. Preferably, the filtration temperature range is from 10° C. to 30° C. Most preferably, between 15° C. and 25° C., which allows improving the purity of the (RS/SR) 1-methylpyrrolidin-3-yl-2-cyclopentyl-2-hydroxy-2-phenylacetate 5-nitroisophthalic acid salt.

The (RS/SR) 1-methylpyrrolidin-3-yl-2-cyclopentyl-2-hydroxy-2-phenylacetate 5-nitroisophthalic acid salt is obtained in very high purity and yields. Yields of the reaction are as good as 70%, and the purity is always very high, being as good as 99.9% and the content of the impurity or not desired (RR/SS) 1-methylpyrrolidin-3-yl-2-cyclopentyl-2-hydroxy-2-phenylacetate 5-nitroisophthalic acid salt is below 1.5%.

Advantageously, the process is easy reproducible at an industrial scale with low energy and costs. In addition, the product is obtained in high yields and high enantiomeric and chemical purity. In addition, the process of the present invention reduces significantly the percentage of the impurity or not desired (RR/SS) 1-methylpyrrolidin-3-yl-2-cyclopentyl-2-hydroxy-2-phenylacetate 5-nitroisophthalic acid salt.

d) Treating the (RS/SR) 1-methylpyrrolidin-3-yl-2-cyclopentyl-2-hydroxy-2-phenylacetate 5-nitroisophthalic acid salt of step b) or c) with a base to yield (RS/SR) 1-methylpyrrolidin-3-yl-2-cyclopentyl-2-hydroxy-2-phenylacetate.

(RS/SR) 1-methylpyrrolidin-3-yl-2-cyclopentyl-2-hydroxy-2-phenylacetate 5-nitroisophthalic acid salt is mixed with an organic solvent and with a base to yield (RS/SR) 1-methylpyrrolidin-3-yl-2-cyclopentyl-2-hydroxy-2-phenylacetate.

Suitable organic solvents that may be used for this step include, but are not limited to: toluene, tetrahydrofuran, methyltetrahydrofuran, xylene, n-heptane, octane, isooctane, cyclohexane, pentane, 1,4-dioxane, isopropylacetate, ethylacetate. Preferably, the organic solvent is isopropylacetate.

Suitable bases that may be used for this step include, but are not limited to: metal hydroxides, such as sodium hydroxide and potassium hydroxide; metal carbonates, such as sodium carbonate and potassium bicarbonate; metal acetates, such as sodium acetate and potassium acetate; ammonia derivatives; such as triethylamine, dicyclohexylamine, N,N-diisopropylethylamine and aqueous ammonia or mixtures thereof. Among them triethylamine, metal hydroxides and metal carbonates are preferred, most preferred in aqueous solution. More preferably, metal carbonates. Most preferably, potassium carbonate.

e) Contacting the (RS/SR) 1-methylpyrrolidin-3-yl-2-cyclopentyl-2-hydroxy-2-phenylacetate of step d) with methyl bromide to yield glycopyrronium bromide.

(RS/SR) 1-methylpyrrolidin-3-yl-2-cyclopentyl-2-hydroxy-2-phenylacetate is reacted with methyl bromide in an organic solvent providing (3RS)-3-[(2SR)-(2-cyclopentyl-2-hydroxy-2-phenylacetyl)oxy]-1,1-dimethylpyrrolidinium bromide (glycopyrronium bromide). Preferably, the reaction is carried out at room temperature. The term "room temperature" in the context of the preparation of glycopyrronium bromide means that the temperature is between 15-30° C. Afterwards, the obtained product is isolated by means of conventional isolation techniques. Preferably, the glycopyrronium bromide is isolated by filtration. Optionally, the glycopyrronium bromide obtained is purified and/or dried.

Suitable organic solvents that may be used for this step include, but are not limited to: ester solvents, such as ethyl formate, methyl acetate, ethyl acetate, isopropyl acetate, ethyl malonate; ketone solvents, such as acetone, methyl ethyl ketone, methyl isobutyl ketone, methyl isopropyl ketone; ether solvents, such as diethyl ether, dipropyl ether, diphenyl ether, tetrahydrofuran, 1,4-dioxane; alcohol solvents, such as methanol, ethanol, 1-propanol, 1-butanol, 1-octanol, benzyl alcohol, phenol, trifluoroethanol, glycerol, ethylene glycol, propylene glycol, m-cresol; acetonitrile and mixtures thereof. In a preferred embodiment the organic solvent is selected from the group consisting of ethyl acetate, isopropyl acetate, acetonitrile, acetone and mixtures thereof. Preferably, the organic solvent is ethyl acetate. In a particular embodiment, the organic solvent may be formed by the combination of two or more organic solvents.

Advantageously, the process is easy reproducible at an industrial scale with low energy and costs. In addition, the product is obtained in high yields and high enantiomeric and chemical purity. Further, the process of the present invention reduces significantly the percentage of the impurity or not desired (RR/SS) 3-(2-cyclopentyl-2-hydroxy-2-phenylacetoxy)-1,1-dimethylpyrrolidin-1-ium bromide at values not more than 0.2%.

f) Optionally, purifying the glycopyrronium bromide of step e) by means of conventional purification techniques.

The process provides glycopyrronium bromide in high enantiomeric and chemical purity and yield and can be easily performed at industrial scale.

g) Optionally, converting the glycopyrronium bromide obtained in step e) or f) into another pharmaceutically acceptable salt or co-crystal.

In the following, the present invention is further illustrated by examples. They should in no case be interpreted as a limitation of the scope of the invention as defined in the claims. Unless indicated otherwise, all indications of percentage are by weight.

EXAMPLES

Example 1: Preparation of (3RS)-3-[(2SR)-(2-cyclopentyl-2-hydroxy-2-phenyl-acetyl)oxy]-1,1-dimethylpyrrolidinium bromide A solution of 5-nitroisophthalic acid (6.7 Kg) in 4:1 acetone:water (34 L) is added at 50° C. to a solution of 1-methylpyrrolidin-3-yl-2-cyclopentyl-2-hydroxy-2-phenylacetate (9.7 Kg, 98.6% HPLC) in 4:1 acetone:water (77 L). The mixture is cooled to 20° C. over a period of 1.5 h, stirred for 1 h and filtered. The wet solid (8.2 Kg dry, 50% yield, 99.7% HPLC, contains 12% of RR/SS mixture) is recrystallized from 5:1 acetone/water (220 L), cooling to 15° C. and stirring for 5 h before filtration. The wet solid (5.7 Kg dry, 70% yield, 99.8% HPLC, contains 5% of RR/SS mixture) is suspended in 5:1 acetone/water (175 L), heated to reflux for 1 h, then cooled to 15° C. and stirred for 24 h. After filtration, the solid is dried providing 1-methylpyrrolidin-3-yl-cyclopentyl-2-hydroxy-2-phenylacetate 5-nitroisophthalic acid salt (4.0 Kg) as a white solid.

Yield: 70%.

Purity (HPLC): 99.9%.

Impurity (RR/SS) 1-methylpyrrolidin-3-yl 2-cyclopentyl-2-hydroxy-2-phenylacetate 5-nitroisophthalic acid salt (HPLC): 1.5%

$^1$H-NMR (300 MHz, DMSO-d6), δ (ppm) 8.84 (1H, t, nitroisophthalic), 8.74 (2H, d, nitroisophthalic), 7.60-7.58 (2H, m, phenyl), 7.31-7.18 (3H, m, phenyl), 5.31 (1H, m), 3.39-3.26 (3H, m), 3.11-3.03 (1H, m), 2.91-2.80 (1H, m), 2.74 (3H, s, Me, RS/SR), 2.39-2.27 (1H, m), 1.83-1.71 (1H, m), 1.63-0.93 (9H, m).

The above obtained salt is suspended in isopropyl acetate (24 L), 15% aq. potassium carbonate (24 L) is added and stirred for 15 min. After phase separation, the organic phase is evaporated, and the oily residue redissolved in ethyl acetate (15 L). Neat methyl bromide (10 eq) is added at 0° C., the mixture is then stirred at 20° C. for 5 h and the suspension filtered, giving 3-(2-cyclopentyl-2-hydroxy-2-phenylacetoxy)-1,1-dimethylpyrrolidin-1-ium bromide (2.0 Kg) as a white solid.

Yield: 63%.

Purity (HPLC): 99.5%.

Impurity RR/SS (HPLC): 0.11%

$^1$H-NMR (300 MHz, D$_2$O), δ (ppm) 7.71-7.67 (2H, m, phenyl), 7.55-7.45 (3H, m, phenyl), 5.57 (1H, m), 3.94-3.77 (2H, m), 3.65-3.60 (2H, m), 3.27-3.16 (1H, m), 3.25 (3H, s, —NMe, RS/SR), 3.09 (3H, s, —NMe, RS/SR), 2.82-2.70 (1H, m), 2.24-2.14 (1H, m, RS/SR), 1.80-1.56 (7H, m), 1.35-1.27 (1H, m).

The invention claimed is:

1. A process for preparing glycopyrronium bromide, or another pharmaceutically acceptable salt of glycopyrronium, wherein the process comprises at least the following steps:
    a) Contacting 1-methylpyrrolidin-3-yl-2-cyclopentyl-2-hydroxy-2-phenylacetate with 5-nitroisophthalic acid in a mixture of organic solvent/water to yield (RS/SR) 1-methylpyrrolidin-3-yl-2-cyclopentyl-2-hydroxy-2-phenylacetate-5-nitroisophthalic acid salt (compound III);
    wherein the ratio of organic solvent to water is at most 10:1 (V/V) and the quantity of 5-nitroisophthalic acid is at least 0.5 mol per 1 mol of 1-methylpyrrolidin-3-yl-2-cyclopentyl-2-hydroxy-2-phenylacetate;
    b) Isolating the (RS/SR) 1-methylpyrrolidin-3-yl-2-cyclopentyl-2-hydroxy-2-phenylacetate 5-nitroisophthalic acid salt obtained in step a) by filtration;
    c) Optionally, purifying the (RS/SR) 1-methylpyrrolidin-3-yl-2-cyclopentyl-2-hydroxy-2-phenylacetate 5-nitroisophthalic acid salt of step b) by means of conventional purification techniques;
    d) Treating the (RS/SR) 1-methylpyrrolidin-3-yl-2-cyclopentyl-2-hydroxy-2-phenylacetate 5-nitroisophthalic acid salt of step b) or c) with a base to yield (RS/SR)

1-methylpyrrolidin-3-yl-2-cyclopentyl-2-hydroxy-2-phenylacetate (compound II); and e) Contacting the (RS/SR) 1-methylpyrrolidin-3-yl-2-cyclopentyl-2-hydroxy-2-phenylacetate of step d) with methyl bromide to yield glycopyrronium bromide (compound I).

2. The process for preparing glycopyrronium bromide according to claim 1, wherein the organic solvent mixed with water in step a) is a polar solvent.

3. The process for preparing glycopyrronium bromide according to claim 2, wherein the organic solvent mixed with water in step a) is selected from the group consisting of methanol, isopropanol, and acetone.

4. The process for preparing glycopyrronium bromide according to claim 3, wherein the organic solvent mixed with water in step a) is acetone.

5. The process according to claim 1, wherein the ratio of organic solvent to water is at most 7:1 (V/V) and the quantity of 5-nitroisophthalic acid is at least 0.5 mol per 1 mol of 1-methylpyrrolidin-3-yl-2-cyclopentyl-2-hydroxy-2-phenylacetate.

6. The process according to claim 5, wherein the ratio of organic solvent to water is at most 5:1 (V/V).

7. The process according to claim 6, wherein the ratio of organic solvent to water is at most 4:1 (V/V).

8. The process according to claim 1, wherein the purification of the (RS/SR) 1-methylpyrrolidin-3-yl-2-cyclopentyl-2-phenylacetate-5-nitro-isophthalic acid salt of step c) is carried out at a temperature between 0° C. and 50° C.

9. The process according to claim 8, wherein the purification of step c) is carried out at a temperature between 15° C. and 25° C.

10. The process for preparing glycopyrronium bromide according to claim 1, wherein the base of step d) is selected from the group consisting of metal carbonates, metal hydroxides, and triethylamine.

11. The process for preparing glycopyrronium bromide according to claim 10, wherein the base is selected from the group consisting of potassium carbonate and potassium hydroxide.

12. The process for preparing glycopyrronium bromide according to claim 11, wherein the base is potassium carbonate.

13. The process for preparing glycopyrronium bromide according to claim 1, wherein the base is in aqueous solution.

14. The process for preparing glycopyrronium bromide according to claim 1, wherein ethyl acetate is present as a solvent in step e).

15. The process of preparing glycopyrronium bromide according to claim 1, further comprising the step f)
purifying the glycopyrronium bromide of step d) by means of conventional purification techniques.

16. The process of preparing glycopyrronium bromide according to claim 1, further comprising step g)
converting the glycopyrronium bromide obtained in step d) or e) into another pharmaceutically acceptable salt or co-crystal.

* * * * *